(12) United States Patent
Huber et al.

(10) Patent No.: US 6,368,478 B1
(45) Date of Patent: Apr. 9, 2002

(54) ELECTROCHEMICAL MEASURING DEVICE WITH AN PLANAR SENSOR SUBSTRATE

(75) Inventors: Wolfgang Huber, Lieboch; Wolf-Dietrich Steinböck, Graz; Günther Pucher, Hengsberg; Bernhard Schaffar; Christoph Ritter, both of Graz, all of (AT)

(73) Assignee: F. Hoffmann La Roche AG, Basel (CH)

( * ) Notice: Subject to any disclaimer, the term of this patent is extended or adjusted under 35 U.S.C. 154(b) by 0 days.

(21) Appl. No.: 09/663,341

(22) Filed: Sep. 15, 2000

(30) Foreign Application Priority Data

Sep. 21, 1999 (AT) .................................................. 1614/99

(51) Int. Cl.[7] .............................................. G02N 27/26
(52) U.S. Cl. ........................ 204/409; 204/403; 204/416
(58) Field of Search .............................. 204/400, 403, 204/416, 412, 409

(56) References Cited

U.S. PATENT DOCUMENTS

| 5,284,568 A | 2/1994 | Pace et al. | 204/403 |
| 5,520,787 A | 5/1996 | Honagan et al. | 204/409 |
| 6,001,228 A | 12/1999 | Huber et al. | 204/403 |

FOREIGN PATENT DOCUMENTS

| EP | 0690134 | 1/1996 |
| EP | 0846947 | 6/1998 |

*Primary Examiner*—T. Tung
*Assistant Examiner*—Alex Noguerola
(74) *Attorney, Agent, or Firm*—Dykema Gossett PLLC

(57) ABSTRACT

An electrochemical measuring device comprises an essentially planar sensor substrate with at least one electrochemical sensor, and a cover part in which a tunnel-shaped measuring channel is formed. At least one guiding groove is provided in parallel with the measuring channel. A sealing element which is positioned between the sensor substrate and the cover part to seal the measuring channel is provided with guiding bodies along its length, at least one of which guiding bodies projects into the guiding groove of the cover part. The sealing element is provided with narrow sealing lips bounding the measuring channel. Each short side of the sealing element has a guiding body projecting into recesses in the sensor substrate. The guiding bodies are disposed on that side of a sealing plane defined by the sealing lips, which faces away from the cover part.

6 Claims, 4 Drawing Sheets

PRIOR ART

ELECTROCHEMICAL MEASURING DEVICE WITH AN PLANAR SENSOR SUBSTRATE

BACKGROUND OF THE INVENTION

The present invention relates to an electrochemical measuring device comprising an essentially planar sensor substrate with at least one electrochemical sensor, and a cover part in which a tunnel-shaped flow or measuring channel is formed, at least one guiding groove being provided in parallel with the flow channel, and a sealing element which is positioned between the sensor substrate and the cover part to seal the flow channel, said sealing element featuring guiding bodies along its long side, at least one of which guiding bodies projects into the guiding groove of the cover part, and narrow sealing lips bounding the flow channel being an integral part of the sealing element.

For diverse reasons, such as minimization of costs, miniaturization or automation, the measuring device often includes a plurality of sensors which are positioned on a planar sensor substrate. The advantage of this arrangement is that thin film or thick film techniques may be employed to produce the sensitive regions of the sensors and their contact leads.

If this kind of sensor substrate with the sensors disposed thereon is designed for integration into a flow channel, the flow channel must be formed above the planar sensor substrate with the use of a further part, the arrangement usually resulting in a tunnel-shaped cross-section of the flow channel.

If several such measuring devices are to be used side by side or if such a measuring device is to be inserted in an analyzer, where corresponding means are provided for sample inlet and outlet, the problem will arise that as a rule a sample channel of circular cross-section must be connected to a flow channel of tunnel-shaped cross-section.

This problem is aggravated by the necessity of providing a seal between the sensor substrate and the upper part or cover forming the actual flow channel. Seals can be achieved in various ways.

In U.S. Pat. No. 5,520,787, for example, a flow cell is described, which is bounded by two essentially flat plates, where the individual parts are bonded to each other by means of an adhesive. In between the two plates a spacer is disposed which is made of sealing material. A groove in the spacer is designed to provide the flow channel. A disadvantage of this configuration is that the accurate position of the lateral edge of the flow channel—and hence the filling volume—is not defined. In addition, contact between the adhesive layer and the medium to be determined or the sensors cannot be excluded. With certain measuring processes or test media such contacts are highly undesirable. Furthermore, adhesive vapors during the production process may constitute a serious hazard for the quality of the sensors.

Furthermore, the individual parts of the measuring device may be thermally sealed. This may also be critical—especially in the instance of heat-sensitive substances in the sensor (enzyme sensors, for example). Use of a thermal sealing technique may moreover interrupt or destroy all conductive paths located at a right angle to the flow channel. This implies that thermal sealing techniques can only be used if the sensors are contacted via through-holes from below, which will require considerable manufacturing efforts.

Using an elastomer seal as disclosed in EP 0 690 134 A, for example, has proved to be a more suitable method. It includes an electrochemical flow cell in which a measuring chamber is formed by a recess in a structural part, which is covered by an electrode plate on the opposite side. For sealing purposes a seal element with an opening is provided, the opening essentially corresponding to the recess forming the measuring chamber. These parts are contained in a multi-piece housing which is finally sealed. Two sides of the sealing element carry a bulged rim projecting into a recess on the housing containing the flow cell. For assembly of the flow cell it is a disadvantage that the seal is not held in a defined position in the upper part of the housing before the sensor substrate is inserted. Moreover, it is not fixed in position in the region of sample inlet and outlet.

An electrochemical measuring device of the above kind is disclosed in EP 0 846 947 A. An oblong sealing element is described, which is designed for lateral sealing of a flow channel, and which exhibits a narrow sealing lip extending around the side of the flow channel, whose thickness is about 150 $\mu$m, so that only a very small portion of the surface of the flow channel is bounded by an elastomer part. The position of the seal is precisely defined by means of lateral guiding bodies, which project into corresponding guiding grooves formed in the cover part in parallel with the flow channel. A rib pressing the sealing lips against the sensor substrate is molded integral with the cover part both on the long and short sides of the sealing element and will result in discontinuities in the shape of the flow channel in the region of the sample inlet and outlet.

SUMMARY OF THE INVENTION

It is an object of this invention to further develop an electrochemical measuring device based on the device described above in such a way that an optimum shape of the flow channel will be achieved inside the measuring device while ensuring optimum alignment of the seal and satisfactory positioning of the sealing lips.

According to the invention this object is achieved by proposing that each of the short sides of the sealing element have a guiding body projecting into a recess in the sensor substrate, which guiding bodies are disposed on that side of a sealing plane defined by the sealing lips, which faces away from the cover part. As the guiding grooves cannot be completely relocated to the sensor substrate due to the fact that the existence of a groove would not permit producing the electrical leads by means of planar large-scale production techniques, the invention provides that at least those guiding bodies be relocated to the other side of the sealing plane, which are positioned in the region of the sample inlet or outlet. By configuring the short sides of the sealing element as defined by the invention the axis of sample inlet and outlet can be brought closer to the surface of the sensor substrate, so that the step between the tunnel-shaped cross-section of the flow or measuring channel and the circular cross-section of the sample inlet and outlet will be advantageously reduced. In this way a more homogeneous shape of the cavity will be achieved, which will greatly reduce the formation of air bubbles and facilitate cleaning of the sample channel.

An enhanced variant of the invention provides that two longitudinal guiding bodies be used, which are disposed on the side of the sealing plane facing towards to the cover part, and both ends of which have moulded-on projections pointing towards the axis of the sample channel, which overlap at least partially the guiding bodies positioned on the short side of the sealing element. This will lead to a robust sealing element which during assembly of the measuring device can simply be held in place in the corresponding guiding grooves of the cover part. In this variant a third longitudinal guiding body of the sealing element can be provided on the opposite side of the sealing plane, which will project into a guiding groove in the sensor substrate.

The invention further provides that the inlet and outlet means for the sample medium be positioned between the projections on the ends of the longitudinal guiding bodies.

According to another variant of the invention two longitudinal guiding bodies of the sealing element are positioned on opposite sides of the sealing plane, one guiding groove for one longitudinal guiding body being disposed in the sensor substrate in parallel with the axis of the flow channel.

BRIEF DESCRIPTION OF THE DRAWINGS

The subject of the invention will now be explained with reference to the embodiments described in the drawings, where.

DETAILED DESCRIPTION OF THE PREFERRED EMBODIMENTS

Figure 1:
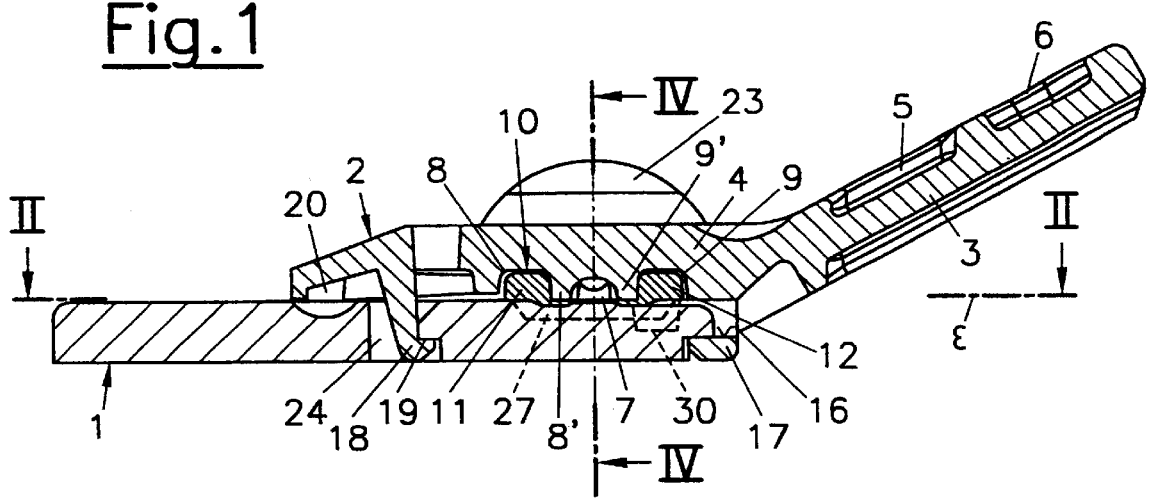
FIG. 1 is a section through the measuring device according to the invention along line I—I in FIG. 2.
Figure 2:
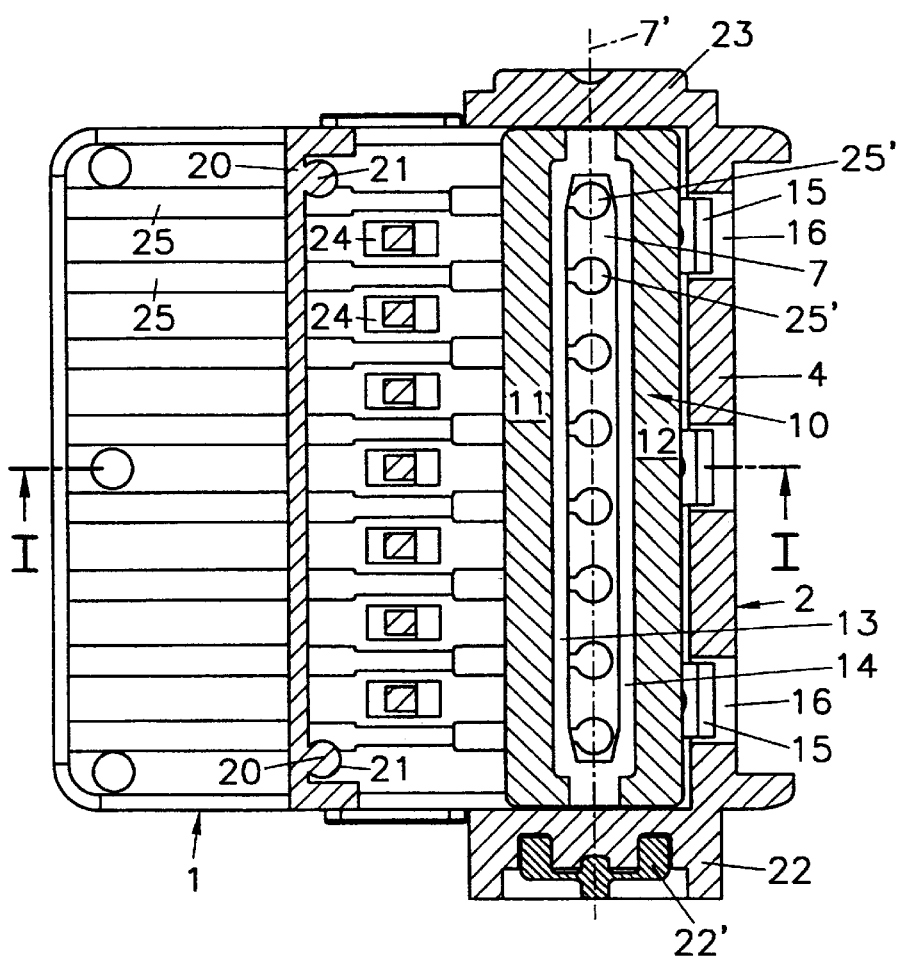
FIG. 2 is a section along line II—II in FIG. 1.

According to FIGS. 1 and 2 the measuring device proposed by the invention comprises a sensor substrate 1 and a cover part 2. The sensor substrate 1 essentially is configured as a planar element. The cover part 2 has a handle 3 to facilitate handling, which projects upwardly at an obtuse angle from the actual cover 4 and is provided with recessed grips 5 and 6. In the cover 4 the flow or measuring channel 7 is configured as a tunnel-shaped groove which extends in longitudinal direction and is open towards the sensor substrate 1. In parallel with the flow channel 7 guiding grooves 8 and 9 are provided in the cover part 2 to receive the guiding bodies 11, 12 of a sealing element 10. The longitudinal guiding bodies 11 and 12 each are provided with a narrow sealing lip 13, 14, which is pressed against the sensor substrate 1 by means of lateral ribs 8', 9'. The sealing lips 13, 14 meeting at the short sides will provide the actual seal between the sensor substrate 1 and the cover part 2.

Figure 4:
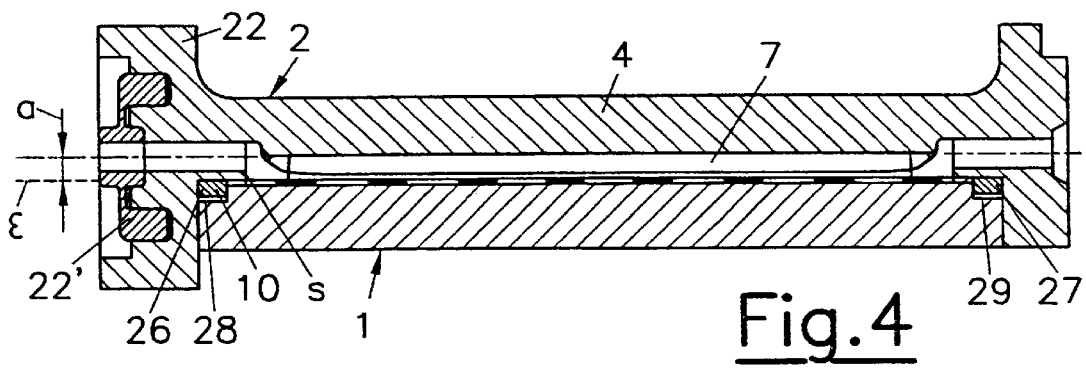
FIG. 4 is a section along line IV—IV in FIG. 1.

The sealing element 10 is provided with guiding bodies 26, 27 on each short side, which project into recesses 28, 29 in the sensor substrate 1 (see FIG. 4). With reference to a sealing plane ϵ defined by the sealing lips 13 and 14, the guiding bodies 11, 12 on the long side and the guiding bodies 26, 27 on the short side are disposed on opposite sides of the sealing plane ϵ.

Figure 3:
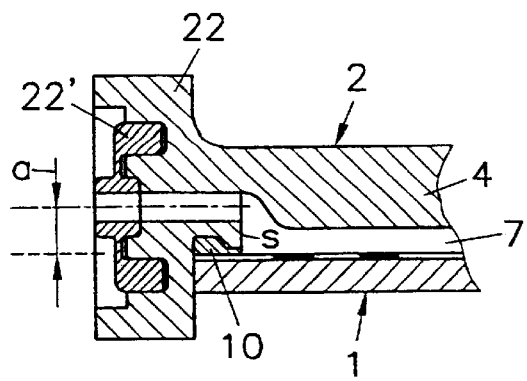
FIG. 3 is a sectional representation of the region of the sample inlet in a known device.
Figure 5:
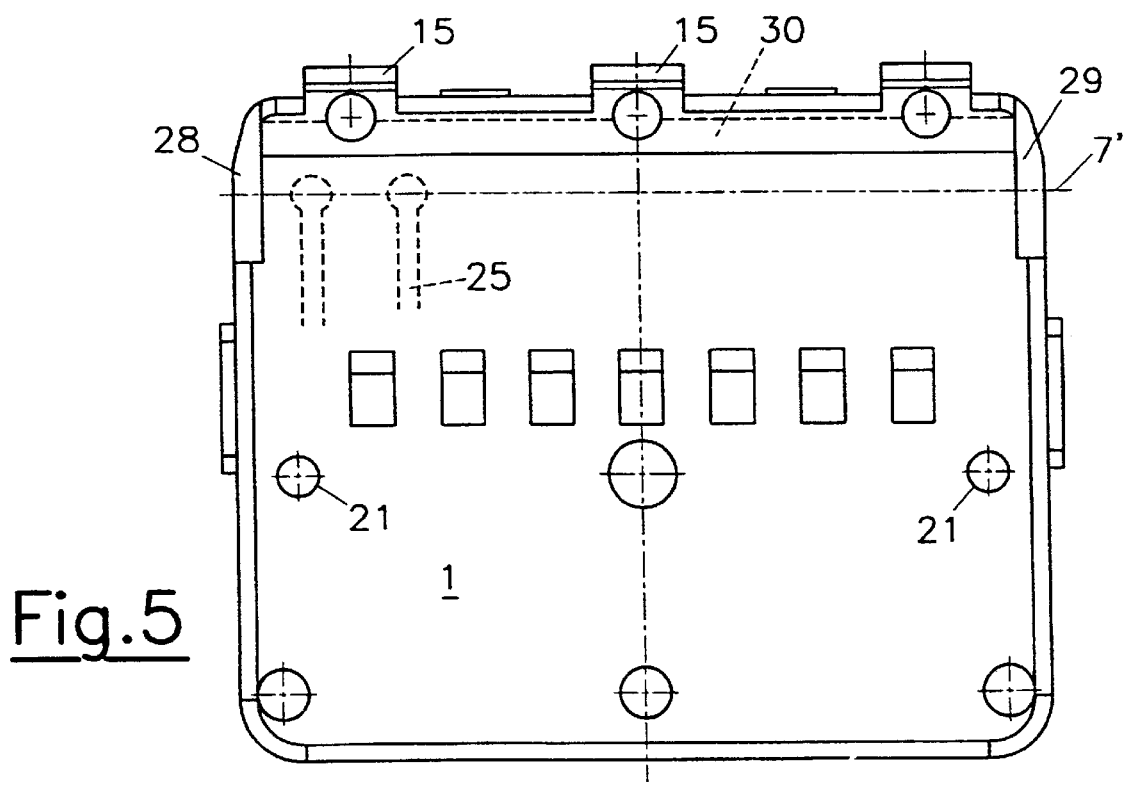
FIG. 5 is a plan view of the sensor substrate.

As is seen in FIGS. 3 (state of the art) and 4 (invention), relocating the guiding bodies 26, 27 of the short side to corresponding recesses 28, 29 of the sensor substrate 1 will lead to a reduction of the distance a between the axis of the sample inlet and/or outlet and the surface of the sensor substrate 1 approximately by half, which in turn will considerably reduce the step s at the transition between the circular cross-section of sample inlet and/or outlet and the tunnel-shaped cross-section of the sample channel 7. The recesses 28, 29 in the sensor substrate 1 designed to hold the guiding bodies 26, 27 are shown in a view from above in FIG. 5.

Some variants (see FIG. 8, FIG. 9, for example) provide that one longitudinal guiding body 32 of the sealing element is positioned parallel to the axis 7' of the measuring channel in a guiding groove 30 of the sensor substrate 1 (indicated by broken lines in FIGS. 1 and 5), while another longitudinal guiding body 11, i.e., the one in the region of the conductive paths 25, remains in the cover part 2.

Figure 6:
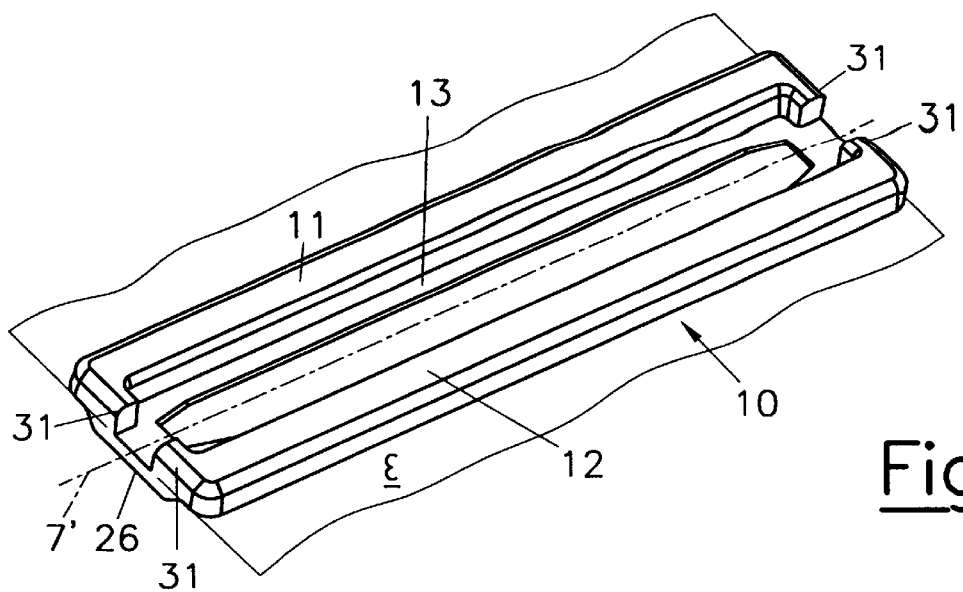
FIGS. 6 and 7 are three-dimensional representations of a first variant of the sealing element in the measuring device provided by the invention.
Figure 7:
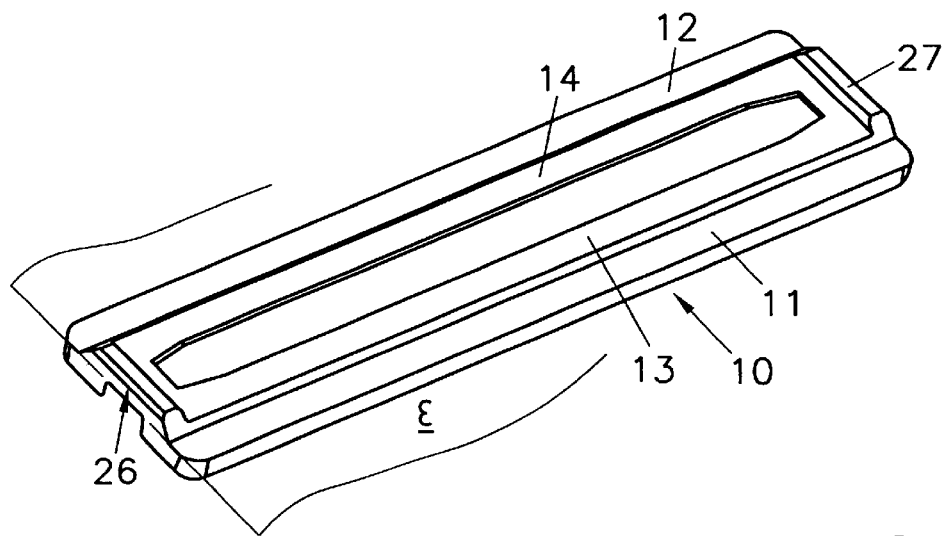

In FIGS. 6 and 7 the sealing element 10 is presented in a three-dimensional view from above and below, respectively. The guiding bodies 11 and 12 may carry integrally molded projections 31 on both ends, which are directed towards the axis 7' of the measuring channel and are designed to partially overlap the short-side guiding bodies 26, 27 on the opposite side of the sealing plane ϵ. In this variant the inlet and outlet means for the medium to be analyzed are disposed between the projections 31 at the ends of the longitudinal guiding bodies 11 and 12.

Figure 8:
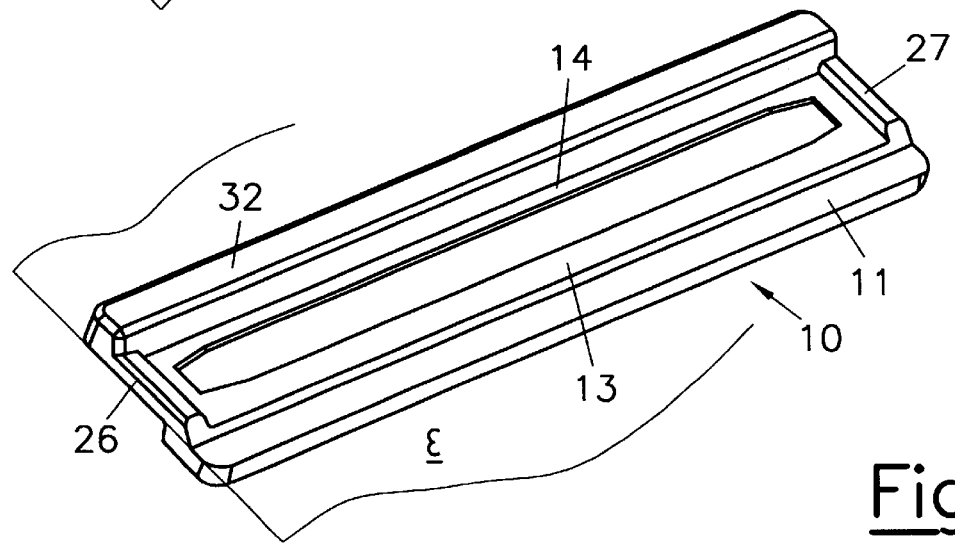
FIGS. 8 and 9 are further variants of the sealing element.

In the variant according to FIG. 8 the two longitudinal guiding bodies 11 and 32 of the sealing element 10 are located on opposite sides of the sealing plane ϵ, guiding body 32 projecting into the guiding groove 30 of the sensor substrate 1.

Figure 9:
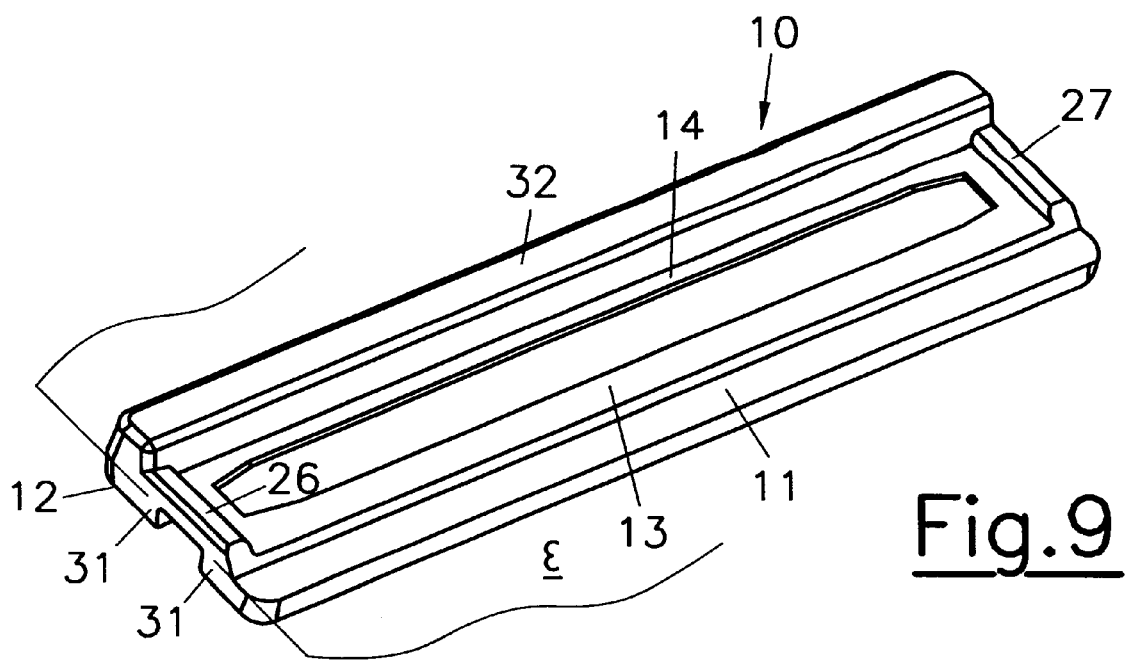

FIG. 9 shows yet another variant of the sealing element 10, with two longitudinal guiding bodies 11, 12 on the same side of the sealing plane ϵ and a third guiding body 32 on the other side.

The sensor substrate 1 and the cover part 2 are connected by a row of locking noses 15 (see FIGS. 1 and 2), which are situated in a straight line along an edge of the sensor substrate 1 and engage a row of corresponding locking surfaces 16. The locking surfaces 16 are formed on the cover part 2 in a ridge 17 extending lengthwise. Once the locking noses 15 engage the locking surfaces 16, the sensor substrate 1 and the cover part 2 are tilted towards each other using the nose 15 as a pivot. Catches 18 which are downwardly projecting from the cover part 2, will lock on to locking surfaces 19 provided in openings 24 of the sensor part 1. Accurate alignment of the sensor part 1 and the cover part 2 is obtained with the use of centering pins 20 projecting from the bottom of the cover part 2, which will extend into center holes 21 on the sensor substrate 1 in the assembled state.

Feeding and draining of the sample medium takes place via inlet and outlet means 22 and 23, respectively, which are integrated in the cover part 2 at an end of the flow channel 7 each.

In the examples presented here the sensor substrate 1 includes eight conductive paths 25, each of which leads to a sensor 25', which may be applied to the plane surface by well-known thick and thin film techniques, such as sputtering, screen-printing, dispensing, etc. The conductive paths will at the same time provide the contacts for the sensors. The openings 24 through which the catches 18 will enter, are located between two conductive paths 25 each.

The present invention will permit a most simple design of a measuring chamber for planar sensor analysis, where the flow channel has a precisely defined geometry and does not include any undesirable materials. The sensor substrate 1 and the cover part 2 may be made from transparent or translucent material to give a good view of the sample in addition to permitting light to enter from the bottom, if required.

The flow or measuring channel 7 has a length of about 1 mm to 70 mm, i.e, preferably 5 mm to 40 mm, and a width of 0.1 to 3 mm, and a depth of 0.1 to 3 mm. Preferably its width and depth are about 1.5 mm. This will give a volume for the flow channel of about 1 to 200 $\mu$l, and preferably 20 to 50 $\mu$l. The sealing lip has a thickness of 50 to 300 $\mu$m, and preferably a thickness of 150 $\mu$m.

The device proposed by the invention is excellently suited for diagnostic purposes, above all for analyses of blood plasma, serum and urine.

What is claimed is:

1. An electrochemical measuring device comprising:

an essentially planar sensor substrate which carries on an upper surface thereof at least one electrochemical sensor; a cover part which provides on a lower surface thereof a tunnel-shaped measuring channel, having at least one guiding groove being provided in parallel with said measuring channel; and a sealing element positioned between said sensor substrate and said cover part when attached together for sealing said measuring channel, said sealing element having long and short sides comprising longitudinal guiding bodies along each of said long sides, at least one of said longitudinal guiding bodies projects into said at least one guiding groove of said cover part, said sealing element comprising integrally molded narrow sealing lips bounding said measuring channel;

wherein each of said short sides of said sealing element is provided with a guiding body projecting into recesses in said sensor substrate, said guiding bodies are disposed on one side of a sealing plane $\epsilon$ defined by said narrow sealing lips which faces away from said cover part.

2. A measuring device according to claim 1, wherein two of said longitudinal guiding bodies are provided, which are disposed on one side of said sealing plane $\epsilon$ facing towards to said cover part, and both ends of said longitudinal guiding bodies have moulded-on projections pointing towards a central axis of said measuring channel, overlapping at least partially said guiding bodies positioned on said short side of said sealing element.

3. A measuring device according to claim 1, wherein said sealing element is provided with a third longitudinal guiding body on an opposite side of said sealing plane $\epsilon$, which projects into a guiding groove situated in said sensor substrate.

4. A measuring device according to claim 2, wherein said sealing element is provided with a third longitudinal guiding body on an opposite side of said sealing plane $\epsilon$, which projects into a guiding groove situated in said sensor substrate.

5. A measuring device according to claim 2, wherein inlet and outlet means for feeding and draining a sample medium to said measuring device are positioned between said molded-on projections on both ends of said longitudinal guiding bodies.

6. A measuring device according to claim 1, wherein two of said longitudinal guiding bodies are provided, which are disposed on opposite sides of said sealing plane $\epsilon$, one of said guiding grooves for one of said longitudinal guiding bodies being disposed in said sensor substrate in parallel with the central axis of said measuring channel.

* * * * *